US006440945B1

(12) United States Patent
Capogrossi

(10) Patent No.: US 6,440,945 B1
(45) Date of Patent: Aug. 27, 2002

(54) METHOD OF INDUCING ANGIOGENESIS IN NONIS CHEMIC SKELETAL MUSCLE

(75) Inventor: Maurizio C. Capogrossi, Rome (IT)

(73) Assignee: Instituto Dermopatico dell'Immacolata, Rome (IT)

( * ) Notice: Subject to any disclaimer, the term of this patent is extended or adjusted under 35 U.S.C. 154(b) by 0 days.

(21) Appl. No.: 09/573,457

(22) Filed: May 17, 2000

Related U.S. Application Data

(60) Provisional application No. 60/136,612, filed on May 27, 1999.

(51) Int. Cl.⁷ ......................... A61K 31/70; C12N 15/63; C12N 15/86; C12N 15/88
(52) U.S. Cl. ..................... 514/44; 435/320.1; 435/455; 435/456; 435/458
(58) Field of Search .................... 514/44; 435/320.1, 435/455–459, 375; 424/93.21

(56) References Cited

U.S. PATENT DOCUMENTS 5,792,453 A    8/1998  Hammond et al. ...... 424/93.21
6,121,246 A    9/2000  Isner

FOREIGN PATENT DOCUMENTS

WO    WO 96/26742      9/1996
WO    WO-98/32859   *  7/1998

OTHER PUBLICATIONS

Safi et al.; Arteriosclerosis/Basic Science/Cardiopulmonary and Critical Care/Circulation/High Bolld Pressure Research/Kidney/Thrombosis, 1996, Circulation vol. 94, No. 8: I-590-I-591.*
Deonarain; Ligand-targeted receptor-mediated vectors for gene delivery, 1998, Exp. Opin. Ther. Patents 8(1): 53-69.*
Verma et al.; Genetherapy-promises, problems and prospects, 1997, Nature vol. 389:239-242.*
Dang et al.; Gene Therapy and Translational Cancer research, 1999, Clinical Cancer Research vo 5: 471-474.*
Bauters et al., *Am. J. Physiol.*, 267, H1263-H1271 (1994).
ES, "Gene implants for vessel-sprouting factor may prevent leg amputations," *Biotechnology Newswatch*, pp. 1 and 8 (Apr. 15, 1996).
Harada et al., *J. Clinic. Invest.*, 94, 623-630 (1994).
Isner et al., *Circulation*, 91 (11), 2687-2692 (1995).
Isner et al., *The Lancet*, 348, 370-374 (1996).
Mack et al., in Direct Myocardial Revascularization: History, Methodology, Technology (Whittaker et al., eds), Chapter 11, 179-200 (Kluwer Academic Publishers, 1999).
Magovern et al., *Hum. Gene Ther.*, 8, 215-227 (1997).
Melillo et al., *Cardiovascular Research*, 35, 480-489 (1997).
Mühlhauser et al., *Hum. Gene. Ther.*, 6, 1457-1465 (1995).
Mühlhauser et al., *Circ. Res.*, 77 (6), 1077-1086 (1995).
Pili et al., *Int. J. Cancer.*, 73, 258-263 (1997).
Safi et al., *J. Mol. Cell Cardiol.*, 29, 2311-2325 (1997).
Safi et al., *Microvascular Research*, 58(3), 238-249 (1999).
Steg et al., *Circulation*, 90(4), 1648-1656 (1994).
Takeshita et al., *Circulation*, 90(5) (part 2), II-228—II-234 (1994).
Takeshita et al., *J. Clinic. Invest.*, 93, 622-670 (1994).
Tsurumi et al., *Circulation*, 94 (12), 3281-3290 (1996).
Wolff et al., *Science*, 247, 1465-1468 (1990).
Wolff et al., *Biotechniques*, 11(4), 474-485 (1991).
Wolff et al., *Hum. Mol. Gen.*, 1(6), 363-369 (1992).

* cited by examiner

Primary Examiner—Dave T. Nguyen
Assistant Examiner—Quang Nguyen
(74) Attorney, Agent, or Firm—Leydig, Voit & Mayer, Ltd.

(57) ABSTRACT

The present invention provides a method for enhancing the level of perfusion of blood to a nonischemic skeletal muscle, e.g., by inducing angiogenesis or collateral blood formation in a nonischemic skeletal muscle at risk of being affected by ischemia or a vascular occlusion, by administration of a pharmaceutical composition comprising a DNA encoding an angiogenic peptide, such that the level of perfusion of blood to the nonischemic skeletal muscle is enhanced.

18 Claims, 7 Drawing Sheets

METHOD OF INDUCING ANGIOGENESIS IN NONISCHEMIC SKELETAL MUSCLE

CROSS-REFERENCE TO RELATED APPLICATIONS

This application claims priority to U.S. patent application Ser. No. 60/136,612, filed on May 27, 1999.

TECHNICAL FIELD OF THE INVENTION

The present invention pertains generally to methods for inducing angiogenesis or collateral blood formation in a nonischemic skeletal muscle at risk of being affected by ischemia or a vascular occlusion, thereby maintaining or enhancing the level of perfusion of blood to the nonischemic skeletal muscle.

BACKGROUND OF THE INVENTION

Vascular atherosclerotic disease, also known as peripheral arterial occlusive disease, is a major health problem, especially in the elderly. Its prevalence increases with age from 3% in individuals younger than 60 years old to over 20% in individuals 75 years or older. Treatment of patients suffering from peripheral arterial occlusive disease remains a considerable clinical issue despite advances in both surgical and percutaneous revascularization techniques. Many patients cannot benefit from these therapies because of the anatomic extent and distribution of arterial occlusion. In such patients, new therapeutic strategies have been sought to prevent the development of disabling symptoms related to ischemia such as claudication, resting pain and loss of tissue integrity in the distal limbs. The latter can ultimately lead to limb loss.

Angiogenesis, the growth of new blood vessels, is a complex process involving disruption of vascular basement membranes, migration and proliferation of endothelial cells, and subsequent blood vessel formation and maturation. Several mediators are known to elicit angiogenic responses, and administration of these mediators promotes revascularization of ischemic tissues. Vascular endothelial growth factor (VEGF) is one of the most specific of the known angiogenic mediators due to localization of its receptors almost exclusively on endothelial cells. Receptors for VEGF are upregulated under ischemic conditions, and the administration of recombinant VEGF augments development of collateral vessels and improves function in peripheral and myocardial ischemic tissue.

The presence of tissue ischemia at the time of administration of an angiogenic mediator has been considered an essential precondition to evoke the desired angiogenic effect. Whether an angiogenic mediator delivered to a normoperfused tissue prior to the occurrence of ischemia could stimulate the neovascularization process and preserve blood perfusion once ischemia develops remains an unsolved issue. Studies have shown, in principle, that it was possible to induce neovascularization in vivo using adenoviral vectors encoding VEGF in nonischemic retroperitoneal adipose tissue and nonischemic subcutaneous tissue. Another study demonstrated that in vivo angiogenesis could be induced by recombinant adenoviral vectors encoding either secreted or nonsecreted forms of acidic fibroblast growth factor (aFGF). Yet, another study failed to find that endothelial cell growth factor (ECGF) had any significant angiogenic effect on vessel growth in nonischemic tissue, yet stimulated vessel growth in ischemic tissue.

In addition to its importance in understanding the basic mechanisms involved in therapeutic angiogenesis, induction of angiogenesis in nonischemic skeletal muscle actually has clinical significance. There are many patients with peripheral arterial disease who do not have chronic ischemia but rather recurrent episodes of ischemia during physical activity. In one study, intermittent claudication was the only complaint in approximately 70% of patients with either aortoiliac or femoropopliteal atherosclerotic involvement.

In view of the foregoing, there exists a need for an effective method of inducing angiogenesis in a nonischemic skeletal muscle. The present invention provides such a method. These and other advantages of the present invention, as well as additional inventive features, will be apparent from the description of the invention provided herein.

BRIEF SUMMARY OF THE INVENTION

The present invention provides a method for enhancing the level of perfusion of blood to a nonischemic skeletal muscle involving administering to a nonischemic skeletal muscle a pharmaceutical composition comprising (a) a pharmaceutically acceptable carrier and (b) a DNA encoding an angiogenic peptide. The present invention further provides a method of treating, either therapeutically or prophylactically, a nonischemic skeletal muscle at risk of suffering from ischemic damage. Also provided is a method of treating a nonischemic skeletal muscle at risk of being affected by a vascular occlusion through induction of collateral blood vessel formation in the nonischemic skeletal muscle. Finally, a method of inducing angiogenesis is provided by the present invention.

BRIEF DESCRIPTION OF THE DRAWINGS

FIG. 3A shows data at day 1 after surgery, FIG. 3B shows data at day 7 after surgery, and FIG. 3C show data at day 14 after surgery. In the graph of each of FIGS. 3A–3C, data are shown at rest (2 min), during stimulation (4–8 min), and during recovery (10–20 min).

FIG. 4A is a bar graph of arteriole length density, and FIG. 4B is a bar graph of capillary length density.

DETAILED DESCRIPTION OF THE INVENTION

Figure 1:
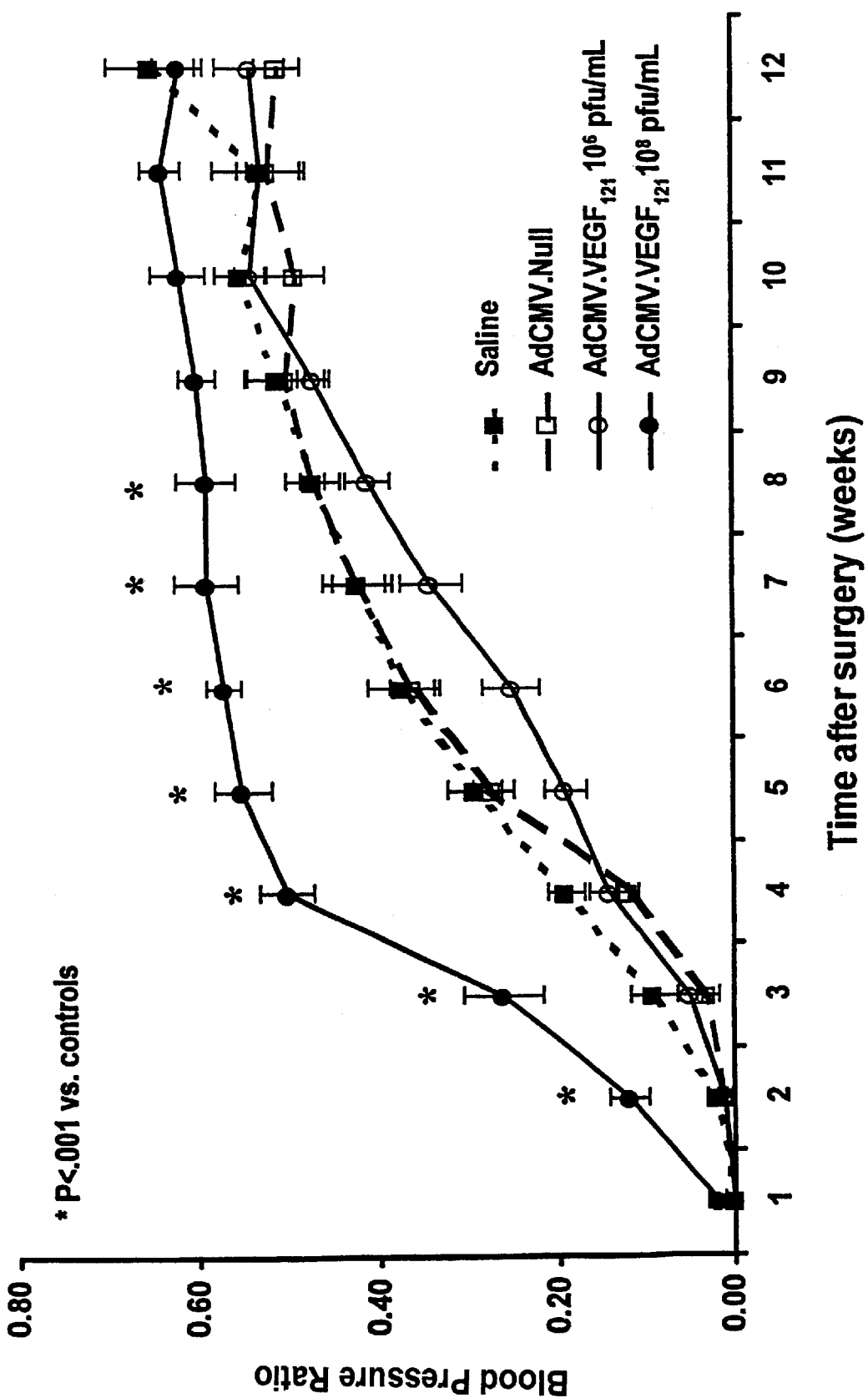
FIG. 1 is a graph of blood pressure ratio (BPR; ischemic/nonischemic limb) versus time after surgery (weeks) of rabbits treated with AdCMV.VEGF$_{121}$ $10^6$ pfu/ml, AdCMV.VEGF$_{121}$ $10^8$ pfu/ml, AdCMV.Null (control), and saline (control).

The invention may best be understood with reference to the following detailed description of the preferred embodiments. The present invention provides a method for enhancing the level of perfusion of blood to a nonischemic skeletal muscle involving administering to a nonischemic skeletal muscle a pharmaceutical composition (e.g., a dose thereof) comprising (a) a pharmaceutically acceptable carrier and (b) a DNA encoding an angiogenic peptide. The present invention further provides a method of treating, either therapeutically or prophylactically, a nonischemic skeletal muscle at risk of suffering from ischemic damage. Also provided is a method of treating a nonischemic skeletal muscle at risk of being affected by a vascular occlusion through induction of collateral blood vessel formation in the nonischemic skeletal muscle. Finally, a method of inducing angiogenesis is provided by the present invention.

Induction of Angiogenesis

By the term "inducing angiogenesis" or "induction of angiogenesis," it is meant that angiogenesis is either initiated or enhanced. Therefore, for example, when the nonischemic skeletal muscle is not already undergoing angiogenesis, the present method provides for initiation of angiogenesis in the nonischemic skeletal muscle. However, when the nonischemic skeletal muscle is already undergoing angiogenesis, the present method provides a means by which the level of angiogenesis is enhanced or heightened.

Nonischemic Skeletal Muscle

Any suitable nonischemic skeletal muscle can be subject to administration within the context of the present invention. Preferably, the nonischemic skeletal muscle comprises receptors capable of binding the angiogenic peptide encoded by the DNA; more preferably, the nonischemic skeletal muscle comprises VEGF receptors. Generally, the nonischemic skeletal muscle will be part of a discrete organ, such as a limb.

Typically, the nonischemic skeletal muscle will be at risk of suffering from ischemic damage, which results when tissue is deprived of an adequate supply of oxygenated blood. An interruption in the supply of oxygenated blood is often caused by a vascular occlusion. Vascular atherosclerotic disease, other diseases, trauma, surgical procedures, and/or other indications can cause such vascular occlusion in nonischemic skeletal muscle.

There are many ways to determine if nonischemic skeletal muscle is at risk of suffering ischemic damage from an undesirable vascular occlusion. Such methods are well known to physicians who treat such conditions, and include clinical evaluation (history and physical examination), Doppler, treadmill test to evaluate time to development of symptoms (e.g., pain), CT scan, NMR angiography, $^{31}$P NMR spectroscopy, and contrast angiograms. Induction of angiogenesis in nonischemic skeletal muscle at risk of being affected by a vascular occlusion is an effective means of preventing and/or attenuating any resulting ischemia. As a result, although any suitable nonischemic skeletal muscle can be targeted for the induction of angiogenesis, the target nonischemic skeletal muscle preferably is one that is at risk of being affected by a vascular occlusion.

DNA Encoding an Angiogenic Peptide

Any DNA encoding an angiogenic peptide operably linked to suitable expression signals can be used within the context of the present invention. Preferably, the angiogenic peptide is a VEGF protein, and more preferably, the angiogenic peptide is $VEGF_{121}$, $VEGF_{145}$, $VEGF_{165}$, $VEGF_{189}$, or a mammalian counterpart, which are variously described in U.S. Pat. No. 5,332,671 (Ferrara et al.), U.S. Pat. No. 5,240,848 (Keck et al.); and U.S. Pat. No. 5,219,739 (Tischer et al.). Most preferably, because of their higher biological activity, the angiogenic peptide is $VEGF_{121}$ or $VEGF_{165}$, particularly $VEGF_{121}$. A notable difference between $VEGF_{121}$ and $VEGF_{165}$ is that $VEGF_{121}$ does not bind to heparin with a high degree of affinity, as does $VEGF_{165}$. Generally, VEGF moieties are advantageous over other angiogenic peptides because VEGF proteins do not induce the growth of tissues not involved in the production of new vasculature. Other angiogenic peptides include VEGF II, VEGF-C, fibroblast growth factors (FGFs) (e.g., aFGF, bFGF, and FGF-4), angiopoiteins, angiogenin, angiogenin-2, and P1GF, which are variously described in U.S. Pat. No. 5,194,596 (Tischer et al.), U.S. Pat. No. 5,219,739 (Tischer et al.), U.S. Pat. No. 5,338,840 (Bayne et al.), U.S. Pat. No. 5,532,343 (Bayne et al.), U.S. Pat. No. 5,169,764 (Shooter et al.), U.S. Pat. No. 5,650,490 (Davis et al.), U.S. Pat. No. 5,643,755 (Davis et al.), U.S. Pat. No. 5,879,672 (Davis et al.), U.S. Pat. No. 5,851,797 (Valenzuela et al.), U.S. Pat. No. 5,843,775 (Valenzuela et al.), and U.S. Pat. No. 5,821,124 (Valenzuela et al.); International Patent Application WO 95/24473 (Hu et al.); European Patent Documents 476 983 (Bayne et al.), 506 477 (Bayne et al.), and 550 296 (Sudo et al.); Japanese Patent Documents 1038100, 2117698, 2279698, and 3178996; and J. Folkman et al., *A Family of Angiogenic Peptides, Nature*, 329, 671 (1987).

Administration of DNA Encoding an Angiogenic Peptide

Induction of angiogenesis via systemic administration of a DNA encoding an angiogenic peptide, such as VEGF, can lead to promiscuous induction of angiogenesis. Promiscuous induction of angiogenesis can cause blindness, increase the aggressiveness of tumor cells, and lead to a multitude of other negative side-effects. To attenuate or prevent such negative side effects, it is desirable to induce angiogenesis only in the tissue in which it is required (i.e., the nonischemic skeletal muscle).

The present invention involves the administration of a DNA encoding the angiogenic peptide in a localized manner to nonischemic skeletal muscle. While any suitable means of administering the DNA encoding the angiogenic peptide to the nonischemic skeletal muscle can be used within the context of the present invention, preferably, such a localized administration to the nonischemic skeletal muscle is accomplished by directly injecting the DNA encoding the angiogenic peptide into the nonischemic skeletal muscle or by topically applying the DNA encoding the angiogenic peptide to the nonischemic skeletal muscle. By the term "injecting," it is meant that the DNA encoding the angiogenic peptide is forcefully introduced into the nonischemic skeletal muscle. Any suitable injection device can be used within the context of the present invention. However, it is desirable that whatever means of administering the DNA encoding the angiogenic peptide is chosen, the induction of angiogenesis in non-targeted tissue is minimized.

For treatment of the hindlimb, the DNA encoding the angiogenic peptide can be delivered, for example, by intramuscular injection or a catheter inserted into the proximal portion of the femoral artery or arteries. For treatment of other nonischemic skeletal muscle, the DNA encoding the angiogenic peptide can be delivered by a catheter or like device inserted sufficiently deeply into the proximal portion of the organ- or tissue-feeding artery or arteries so that gene transfer is effected substantially only into the cells of the target organ or tissue.

Delivery of a DNA encoding an angiogenic peptide remains a significant challenge. The half-life of many of these angiogenic peptides is very short, the administration of high doses of angiogenic peptides is associated with hypotension, and systemic administration of angiogenic peptides can cause promiscuous induction of angiogenesis in tissues other than that which has been targeted. Furthermore, the quantity of angiogenic peptide delivered is important. If too little angiogenic peptide is delivered, angiogenesis will not be induced, and a significant therapeutic benefit will not be achieved. If too much angiogenic peptide is delivered, the formation of disorganized vasculature beds, loss of function in the affected tissue, and promiscuous angiogenesis can result.

A number of different delivery methods are available for administering a DNA encoding an angiogenic peptide, including plasmid DNA, plasmid-liposome complexes, and viral vectors. Any suitable viral vector can be used in the context of the present inventive method to administer the DNA encoding an angiogenic peptide. Examples of such suitable viral vectors are adenoviral vectors, herpes simplex viral vectors, and adeno-associated viral vectors.

Plasmids, genetically engineered circular double-stranded DNA molecules, can be designed to contain an expression cassette for delivery of a specific DNA. Although plasmids were the first method described for gene transfer of DNA encoding an angiogenic peptide, their level of efficiency is poor, compared with other techniques. By complexing the plasmid with liposomes, the efficiency of gene transfer in general is improved. While the liposomes used for plasmid-mediated gene transfer strategies have various compositions, they are typically synthetic cationic lipids. The positively charged liposome forms a complex with a negatively charged plasmid. These plasmid-liposome complexes enter target cells by fusing with the plasma membrane. Advantages of plasmid-liposome complexes include their ability to transfer large pieces of DNA encoding an angiogenic peptide and their relatively low potential to evoke immunogenic responses in the host.

The adenovirus is a 36 kb double-stranded DNA virus that efficiently transfers DNA in vivo to a variety of different target cell types, including skeletal muscle. The virus is made suitable by deleting some of the genes required for viral replication; the expendable E3 region is also frequently deleted to provide additional room for a larger DNA insert. The resulting replication deficient adenoviral vectors can accommodate up to 7.5 kb of exogenous DNA and are capable of being produced in high titers and efficiently transferring DNA to replicating and non-replicating cells. Of particular importance for transfer of DNA to the skeletal muscle, in which the host cell is a terminally differentiated cell, is the ability of adenoviral vectors to efficiently transfer DNA to non-replicating cells. The newly transferred genetic information remains epi-chromosomal, thus eliminating the risks of random insertional mutagenesis and permanent alteration of the genotype of the target cell.

The herpes simplex virus (HSV) is another viral vector that can be used to administer a DNA encoding an angiogenic peptide. The mature HSV virion consists of an enveloped icosahedral capsid with a viral genome consisting of a linear double-stranded DNA molecule that is 152 kb. Most replication-deficient HSV vectors contain a deletion to remove one or more intermediate-early genes to prevent replication. Advantages of the herpes vector are its ability to enter a latent stage that could potentially result in long-term DNA expression, and its large viral DNA genome that can accommodate exogenous DNA up to 25 kb.

Adeno-associated virus (AAV) vectors represent other viral vectors that can be used to administer a DNA encoding an angiogenic peptide. AAV is a DNA virus, which is not known to cause human disease and which requires coinfection by a helper virus (i.e., an adenovirus or a herpes virus) for efficient replication. AAV vectors used for administration of a DNA encoding an angiogenic peptide have approximately 96% of the parental genome deleted such that only the terminal repeats remain, which contain recognition signals for DNA replication and packaging. This eliminates immunologic or toxic side effects due to expression of viral genes.

Preferably, administration of the DNA encoding an angiogenic peptide is accomplished using an adenoviral vector. The adenoviral vector is preferably deficient in at least one gene function required for viral replication. Preferably, the adenoviral vector is deficient in at least one essential gene function of the E1 region of the adenoviral genome (e.g., the E1a and/or E1b region), particularly the E1a region. More preferably, the vector is deficient in at least one essential gene function of the E1 region and part of the E3 region (e.g., an XbaI deletion of the E3 region). Alternatively, the vector is deficient in at least one essential gene function of the E1 region and at least one essential gene function of the E4 region. However, adenoviral vectors deficient in at least one essential gene function of the E2a region and adenoviral vectors deficient in all of the E3 region also are contemplated here and are well known in the art. Adenoviral vectors deleted of the entire E4 region can elicit lower host immune responses. Suitable replication deficient adenoviral vectors are disclosed in International Patent Applications WO 95/34671 and WO 97/21826. For example, suitable replication deficient adenoviral vectors include those with a partial deletion of the E1a region, a partial deletion of the E1b region, a partial deletion of the E2a region, and a partial deletion of the E3 region. Alternatively, the replication deficient adenoviral vector can have a deletion of the E1 region, a partial deletion of the E3 region, and a partial deletion of the E4 region.

Furthermore, the adenoviral vector's coat protein can be modified so as to incorporate a specific protein binding sequence, as described in U.S. Pat. No. 5,770,442 (Wickham et al.), or the adenoviral vector's coat protein can be modified so as to decrease the adenoviral vector's ability or inability to be recognized by a neutralizing antibody directed against the wild-type coat protein, as described in International Patent Application WO 98/40509. Other suitable modifications to the adenoviral vector are described in U.S. Pat. No. 5,559,099 (Wickham et al.), U.S. Pat. No. 5,731,190 (Wickham et al.), U.S. Pat. No. 5,712,136 (Wickham et al.), U.S. Pat. No. 5,846,782 (Wickham et al.), U.S. Pat. No. 5,962,311 (Wickham et al.), and U.S. Pat. No. 6,057,155 (Wickham et al.) and International Patent Applications WO 97/20051, WO 98/07877, WO 98/54346, and WO 00/15823.

In addition to including the DNA encoding an angiogenic peptide, the adenoviral vector also can include a DNA encoding another peptide, for example, an angiogenic peptide receptor or another angiogenic peptide. Suitable angiogenic peptide receptors include, for example, FLT-1, FLK-1, and FLT-4.

The DNA, operably linked to expression signals and encoding the angiogenic peptide, can be inserted into any suitable region of the adenoviral vector as an expression cassette. In that respect, the skilled artisan will readily appreciate that there are certain advantages to using an adenoviral vector deficient in some essential gene region of the adenoviral genome inasmuch as such a deficiency will provide room in the vector for a transgene and will prevent the virus from replicating. Preferably, the DNA segment is inserted into the E1 region of the adenoviral vector. Whereas the DNA segment can be inserted as an expression cassette in any suitable orientation in any suitable region of the adenoviral vector, preferably, the orientation of the DNA segment is from right to left. By the expression cassette having an orientation from right to left, it is meant that the direction of transcription of the expression cassette is opposite that of the region of the adenoviral vector into which the expression cassette is inserted.

An adenoviral vector illustrative of the present inventive vector is deficient in the E1a region, part of the E1b region, and part of the E3 region of the adenoviral genome and contains the DNA encoding human $VEGF_{121}$ or human $VEGF_{165}$ under the control of the CMV immediate early promoter in the E1 region of the adenoviral genome. Such a vector supports in vivo expression of VEGF that is maximized at one day following administration and is not detectable above baseline levels as little as one week after administration. This is ideal inasmuch as it is sufficient to provide substantial growth of new vasculature while minimizing adverse neovascularization at distal sites.

Pharmaceutical Composition

The angiogenic peptide desirably is administered to the nonischemic skeletal muscle in a pharmaceutical composition, which comprises a pharmaceutically acceptable carrier and the DNA encoding the angiogenic peptide.

Any suitable pharmaceutically acceptable carrier can be used within the context of the present invention, and such carriers are well known in the art. The choice of carrier will be determined, in part, by the particular site to which the composition is to be administered and the particular method used to administer the composition. Formulations suitable for injection include aqueous and non-aqueous solutions, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous injection solutions and suspensions can be prepared from sterile powders, granules, and tablets ofthe kind previously described. Preferably, the pharmaceutically acceptable carrier is a buffered saline solution.

In addition, the pharmaceutical carrier also can contain peptides, for example, an angiogenic peptide receptor, an angiogenic peptide, or a factor necessary for the development of blood vessels. These additional peptides can be encoded by a DNA, which can be a plasmid or contained within a viral vector (e.g., HSV, adenovirus, or AAV). It should be appreciated that a plasmid or viral vector comprising the DNA encoding an angiogenic peptide can be the same or different than the plasmid or viral vector that comprises the DNA encoding these additional peptides.

Although any suitable volume of carrier can be utilized within the context of the present invention, preferably, the DNA encoding the angiogenic peptide is administered in small volumes of carrier. Administration of small volumes is such that the tissue to be vascularized (i.e., the nonischemic skeletal muscle) is perfused with the DNA encoding the angiogenic peptide and very little or no DNA encoding the angiogenic peptide is carried by the blood, lymphatic drainage, or physical mechanisms (e.g., gravitational flow or osmotic flow) to tissues not targeted.

Dosage

Those of ordinary skill in the art can easily make a determination of proper dosage of the DNA encoding the angiogenic peptide. However, generally, certain factors will impact the dosage that is administered.

The proper dosage is such that the level of perfusion is enhanced to the nonischemic skeletal muscle. Preferably, the dosage is sufficient to have a therapeutic and/or prophylactic effect on nonischemic skeletal muscle that is at risk of being affected by ischemia or a vascular occlusion. Additionally, the dosage should be such that induction of angiogenesis in non-targeted tissue is minimized. The dosage also will vary depending upon the angiogenic peptide. Specifically, the dosage will vary depending upon the particular method of administration, including the nature of the vector and DNA encoding and controlling the expression of the angiogenic peptide.

For example, for an adenoviral vector comprising a DNA encoding an angiogenic peptide, a dose typically will be at least about $1\times10^6$ pfu (e.g., $1\times10^6-1\times10^{13}$ pfu) to the nonischemic skeletal muscle, for example, a human hindlimb. The dose preferably is at least about $1\times10^7$ pfu (e.g., about $1\times10^7-1\times10^{13}$ pfu), more preferably at least about $1\times10^8$ pfu (e.g., about $1\times10^8-1\times10^{11}$ pfu), and most preferably at least about $1\times10^9$ pfu (e.g., about $1\times10^9-1\times10^{10}$ pfu). The dose typically is for a volume of targeted tissue of about 100 cm$^3$, more typically about 150 cm$^3$.

For purposes of considering the dose in terms of particle units (pu), also referred to as viral particles, it can be assumed that there are 100 particles/pfu (e.g., $1\times10^{12}$ pfu is equivalent to $1\times10^{14}$ pu). In a single round of vector administration, using, for example, an adenoviral vector deleted of the E1a region, part of the E1b region, and part of the E3 region of the adenoviral genome, wherein the vector carries human $VEGF_{121}$ or $VEGF_{165}$ under the control of a standard CMV immediate early promoter, about $10^7-10^{13}$ pfu, preferably about $10^9-10^{11}$ pfu, are administered to a targeted tissue (e.g., to a discrete organ containing the targeted nonischemic skeletal muscle) with an estimated volume of about 150 cm$^3$. Under these conditions, a substantial level of VEGF production is achieved in the nonischemic skeletal muscle without producing detectable levels of VEGF production in distal tissues.

EXAMPLES

The invention can be more clearly understood with reference to the following examples. The following examples further illustrate the present invention, but should not be construed as in any way limiting its scope.

General Procedures

Subjects

A total of 112 6-month-old male New Zealand White rabbits (HRP Inc. Rabbitry, Denver, Pa.), mean weight 4.0±0.2 kg, and 36 10-month-old male Wistar rats (Wistar Rats Colony, Gerontology Research Center, NIA, NIH, Baltimore, Md.), mean weight 550±50 g, were used in the experimental protocols.

Adenovirus Vectors

The replication-deficient recombinant adenovirus vectors containing the cDNA for $VEGF_{121}$ were engineered according to a technique previously described and were supplied by GenVec, Inc. (Gaithersburg, Md). Briefly, the AdCMV.$VEGF_{121}$ is an E1a$^-$, partial E1b$^-$, partial E3$^-$ adenovirus vector that carries an expression cassette in the E1 position containing the CMV immediate early promoter/enhancer driving the cDNA for the 121-residue form of human VEGF. AdCMV.Null, used as a control vector in this study, is similar to AdCMV.$VEGF_{121}$ but with no gene in the expression cassette.

Intramuscular Administration of AdCMV.$VEGF_{121}$

Four weeks before the induction of ischemia, rabbits were randomly assigned to receive AdCMV.$VEGF_{121}$ ($10^6$ pfu/ml or $10^8$ pfu/ml), AdCMV.Null (as a control) ($10^8$ pfu/ml), or saline (also as a control). Rats received injections of AdCMV.VEGF$_{121}$ ($2\times10^9$ pfu/ml) or AdCMV.Null (as a control) ($2\times10^9$ pfu/ml) two weeks before surgery. The adenovirus vectors were stored in dialysis buffer solutions at $-70°$ C. Each solution for injection was prepared immediately before use and given intramuscularly (IM) in four different sites in the thigh (250 μl/injection, 1 ml total volume in rabbits; 125 μl/injection, 0.5 ml total volume in rats) along the projection of the femoral artery.

Animal Model of Hindlimb Ischemia

Rabbits were pre-anesthetized with ketamine (50 mg/kg) and xylazine (5 mg/kg), intubated using a laryngoscope and an uncuffed 3.5-neonatal orotracheal tube, and placed under mechanical ventilation. Stable anesthesia was achieved using a mixture of 1.5% isoflurane and oxygen. The surgical procedure to induce unilateral hindlimb ischemia in rats was performed under intraperitoneal anesthesia with ketamine (60 mg/kg) and xylazine (10 mg/kg). Both species underwent a similar surgical procedure as described below.

A longitudinal incision was performed in the thigh, extending distally from the inguinal ligament to a point just above the knee. The femoral artery was dissected free along its entire length, as were all its major branches including the inferior epigastric, deep femoral, lateral circumflex, and superficial epigastric arteries. After further dissecting the popliteal and saphenous arteries distally, the external iliac artery, as well as all of the above arteries, was ligated with 5-0 silk (Ethicon, Inc., Somerville, N.J.). The femoral artery was completely excised from its proximal origin as a branch of the external iliac artery to the point distally where it bifurcates into the saphenous and popliteal arteries. Rabbits received 0.9% normal saline (50 ml IV) during surgery. Rats and rabbits were given post-operatory analgesia (buprenorphine 0.04 mg/kg) twice daily for the first two days after the procedure.

Statistical Analysis

All results are expressed as mean±SEM. Statistical comparisons were performed using ANOVA (BMGP Statistical Software). Analysis of the qualitative angiographic data was determined using a Pearson $X^2$ test.

Example 1

This example demonstrates angiogenesis in a nonischemic skeletal muscle by administration of an adenoviral vector comprising a DNA encoding an angiogenic peptide. Further demonstrated by this example is that perfusion of blood is maintained in the skeletal muscle upon induction of ischemia. Angiogenesis in the hindlimb of rabbits was measured physiologically by calf blood pressure and blood flow measurements with radioactive microspheres and anatomically by post-mortem contrast angiography after administration of the adenoviral vector comprising VEGF$_{121}$ to the nonischemic hindlimb and subsequent induction of ischemia.

Calf Blood Pressure Ratio

For twelve weeks after surgery, calf blood pressure was measured weekly in both hindlimbs of thirty-three rabbits using a Doppler flowmeter (Vascular Mini-Lab III, Parks Medical Electronics, Aloha, Oreg.). On each occasion, under sedation with ketamine (50 mg/kg) and xylazine (5 mg/kg), the hindlimbs were shaved and cleaned, the pulse of the posterior tibial artery was identified using a Doppler probe, and the systolic blood pressure in both limbs was determined according to standard techniques. Briefly, a 2.5 cm wide cuff was applied over the thigh, and the Doppler probe was placed over the posterior tibial artery. The cuff was rapidly inflated to approximately 30 mm Hg above the anticipated systolic pressure and then slowly deflated. The pressure at which the Doppler flow signal reappeared was recorded as the systolic pressure. A single observer, blinded to the treatment regimen, performed all measurements. The calf blood pressure ratio (BPR) was then defined as a ratio of systolic pressure of the ischemic limb to systolic pressure of the normal limb. Thus, the lower the ratio, the more impaired the arterial perfusion of the ischemic limb.

FIG. 1, which is a graph of BPR vs. time after surgery (weeks), shows that the animals reached their final recovery ratio of approximately 0.50–0.60 after treatment with AdCMV.VEGF$_{121}$ at $10^8$ pfu/ml after 4 weeks, AdCMV.VEGF$_{121}$ at $10^6$ pfu/ml after 10 weeks, and the control groups (AdCMV.Null and saline) after 9–12 weeks. Further analysis revealed a faster rate of recovery between weeks 1 and 4 for AdCMV.VEGF$_{121}$ than both controls ($P<0.0001$) and animals treated with AdCMV.VEGF$_{121}$ at $10^6$ pfu/ml ($P<0.001$). The higher BPR in AdCMV.VEGF$_{121}$ at $10^8$ pfu/ml group remained significant until week 8 but became not significant thereafter. In animals treated with AdCMV.VEGF$_{121}$ at $10^6$ pfu/ml, the rate of recovery was not different from controls. Statistical analysis of BPR data revealed that there were significant differences between treatment groups ($P<0.0001$) and a significant effect on recovery time after surgery ($P<0.0001$).

Blood Flow Measurements

The regional blood flow to skeletal muscles in both hindlimbs of sixty-four rabbits was measured using the radioactive microspheres technique at day 1 and then at weeks 1, 4, and 12 after surgery. After pre-medication with ketamine and xylazine, a tracheotomy was performed, and animals were placed under mechanical ventilation with room air. Anesthesia was maintained using sodium pentobarbital IV (10–20 mg/kg). A normal saline infusion (40 ml/h) was given through the marginal ear vein. A catheter (Abbocath-T 18 G) was advanced through the left carotid artery into the descending aorta. The catheter was connected to a withdrawal syringe pump (Model SP210iw, World Precision Instruments, Sarasota, Fla.) for blood collection and to a single channel blood pressure monitor (Model 50110, Stoelting, Wood Dale, Ill.).

The chest was opened at the left fourth intercostal space level, the left heart chambers were exposed, and $3.3\times10^6$ radioactive microspheres (15.5 μm diameter) labeled with $^{51}$Cr (NEN Life Science Products, Boston, Mass.) were injected directly into the left ventricle within a 20-second period. Prior to injection, the vial containing the microspheres was placed in warm water ($40°$ C.) for thirty minutes and then, immediately before injection, vigorously shaken (Daigger Vortex, Model Genie 2, Scientific Industries, Inc., Bohemia, N.Y.) for one minute to assure proper mixing of the beads in the solution. An arterial blood reference sample was withdrawn at a constant rate of 2 ml/min starting thirty seconds before, and continued for ninety seconds after, the injection was completed. Animals then were killed with a sodium pentobarbital overdose, and the entire gastrocnemius muscles of both limbs were removed.

Each muscle was cut in three approximately equal parts (proximal, middle and distal), weighed, and put in 50 ml conical polypropylene tubes (Corning Labware & Equipment, Corning, N.Y.). Twenty ml of 2 M KOH and 10 ml of 2% Tween 80 (Sigma Chemical Co., St. Louis, Mo.) were added to each vial for tissue digestion. After 24 hours at $50°$ C. in a constant temperature shaking water bath, the tissue samples were fully dissolved. All samples then were filtered using glass microfiber filters with 1.6 μm diameter pores (Whatman Filters, Whatman International Ltd., England). The filters containing the microspheres were placed into liquid scintillation vials with 10 ml of liquid scintillation cocktail (CytoScint ES, ICN Biomedical Research Products, Costa Mesa, Calif.). To prevent the occurrence of chemiluminescence in the samples, 1 ml of acetic acid was added to each vial.

The level of radioactivity in each sample was determined using a liquid scintillation counter (Model LS5801, Beckman Coulter, Inc., Fullerton, Calif.). The regional blood flow (ml/min/100 g) was calculated using the formula: $\phi_T=100 (\phi_R A_T)/(A_R W_T)$, where $\phi_T$ is the blood flow in the tissue section, $\phi_R$ is the reference sample withdrawal rate (ml/min), $A_T$ is the activity (CPM) in the tissue, $A_R$ is the activity (CPM) in the arterial blood reference sample, and $W_T$ is the weight (g) of the tissue section.

There were no significant differences in regional blood flow (RBF) between treatment groups or time points in nonischemic limbs (P=0.8 and P=0.6 for effects of treatment and time, respectively). Regional blood flow to ischemic limb gastrocnemius muscle versus treatment and time after surgery is presented in Table 1.

V.VEGF$_{121}$ at $10^8$ pfu/ml, AdCMV.Null, or saline, as previously described. At day 1 after surgery, animals were pre-medicated with ketamine and xylazine, as described previously, and a median laparotomy was performed under anesthesia with sodium pentobarbital. The abdominal aorta was fully exposed and a catheter (Abbocath 20 G) introduced directly into the right common iliac artery. A total of 5,000 units of heparin were given to prevent clot formation. The animal was killed with an overdose of sodium pentobarbital and immediately placed under the fluoroscope (Digimax MP4000 Series III Workstation, Acomma Medical Imaging Inc., Wheeling, Ill.). A total of 5 ml contrast media (Hypaque sodium 50%, diatrizoate sodium, Nycomed Inc., Princeton, N.J.) was injected into the right common iliac artery using an infusion syringe pump (Model 848, Edco Scientific Inc., Chapel Hill, N.C.) at a constant rate of 20 ml/min. Serial images of the ischemic hindlimb were recorded and printed out for further analysis.

Quantitative assessment of new collateral vessel development in the thigh was performed using a grid overlay that comprised 2 mm squares. The films and the grid were scanned into a personal computer with the aid of image processing software (Adobe PhotoShop 5.0, Adobe Systems Incorporated) and then were edited for best quality picture.

TABLE 1

| | Regional Blood Flow (ml/min/100 g) (mean ± SE) | | | |
| --- | --- | --- | --- | --- |
| | Day 1 | Week 1 | Week 4 | Week 12 |
| Saline | 2.78 ± 0.43 | 3.93 ± 0.27 | 6.59 ± 0.33 | 6.67 ± 0.33 |
| AdCMV.Null | 2.97 ± 0.50 | 4.10 ± 0.21 | 6.30 ± 0.17 | 6.44 ± 0.55 |
| AdCMV.VEGF$_{121}$ ($10^6$ pfu/ml) | 5.16 ± 0.10† | 7.26 ± 0.51‡ | 7.96 ± 0.53* | 7.87 ± 0.70* |
| AdCMV.VEGF$_{121}$ ($10^8$ pfu/ml) | 5.69 ± 0.40† | 7.5 ± 0.95 | 8.74 ± 0.84* | 8.79 ± 1.03* |

Figure 2:
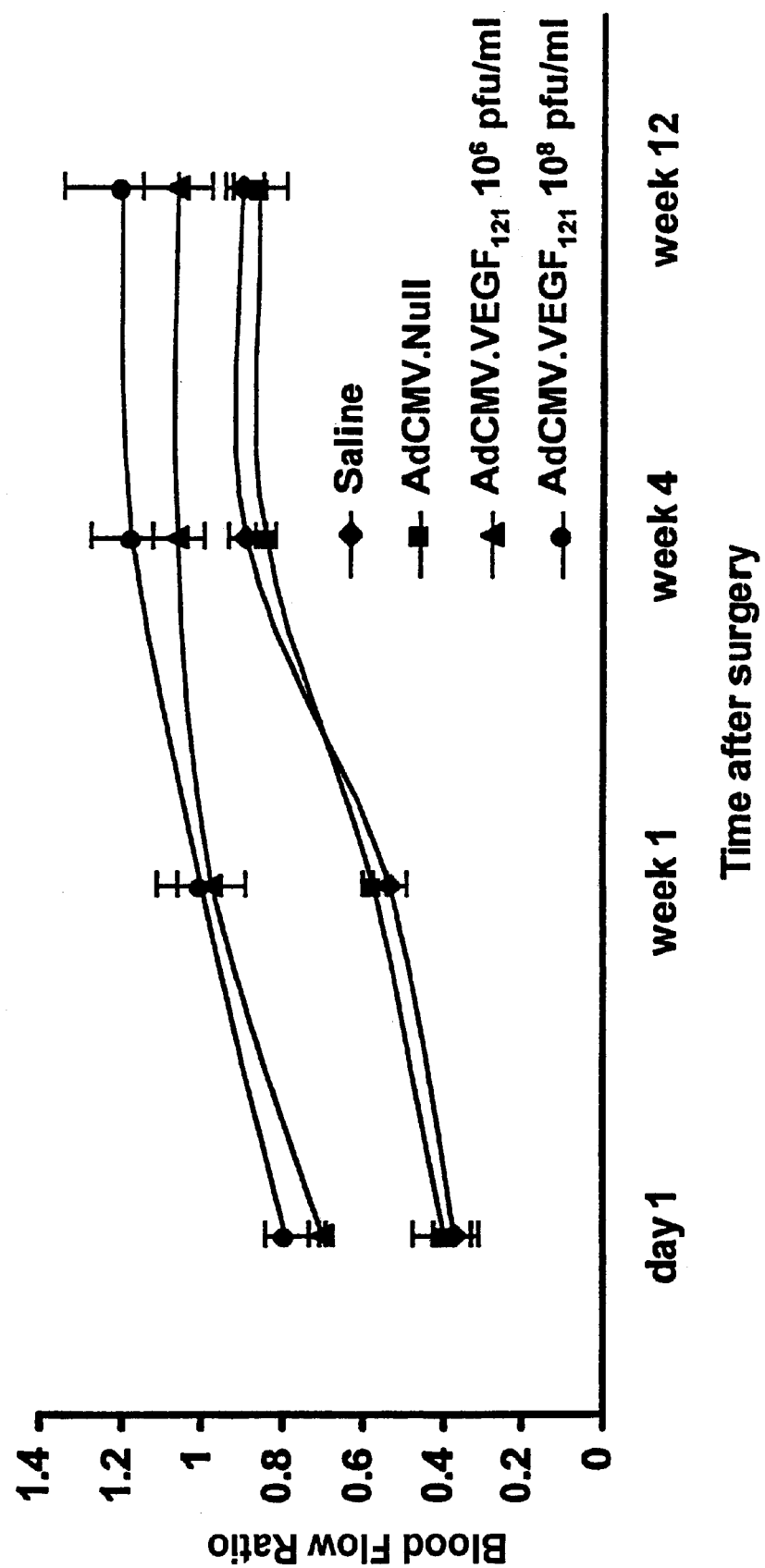
FIG. 2 is a graph of regional blood flow ratio measured by radioactive microspheres (RBF; ischemic/nonischemic limb) versus time after surgery (days and weeks) of the gastrocnemius muscle of rabbits treated with AdCMV.VEGF$_{121}$ $10^6$ pfu/ml, AdCMV.VEGF$_{121}$ $10^8$ pfu/ml, AdCMV.Null (control), and saline (control).

*P < 0.01 vs. both controls,
†P < 0.001 vs. both controls,
‡P < 0.0001 vs. both controls FIG. 2, which is a graph of the calculated ratio between RBF in the ischemic and nonischemic gastrocnemius muscles, shows that animals reached their final recovery ratios of approximately 1.0 and 0.9, for AdCMV.VEGF$_{121}$ and the controls, respectively, after treatment with AdCMV.VEGF$_{121}$ (at $10^6$ or $10^8$ pfu/ml) after 1 week, and the controls (AdCMV.Null and saline) after 4 weeks. Significant differences were found between treatment groups and between time points for RBF in the ischemic limb (P<0.0001 for both effects of time and treatment). As seen in Table 1, RBF in the ischemic limb exhibited nearly a two-fold increase in AdCMV.VEGF$_{121}$-treated animals relative to controls as early as day 1 after surgery (P<0.001). A significant difference in RBF as between AdCMV.VEGF$_{121}$-treated animals and the control animals persisted at all subsequent time points (P<0.01). In addition, the RBF ratio at day 1 after surgery (see FIG. 2) was significantly higher in AdCMV.VEGF$_{121}$-treated animals than in controls, and by week 1, the RBF ratio of the AdCMV.VEGF$_{121}$-treated animals was one, thereby indicating a complete restoration of tissue perfusion.

Contrast Angiography

To anatomically evaluate the development of collateral arteries, conventional post-mortem angiograms of the ischemic limbs of fifteen rabbits were obtained after pre-treatment with intramuscular (IM) injections of AdCM- The angiographic score was determined by direct counting of the total number of contrast-opacified vessels crossing the squares divided by the total number of squares in the pre-defined area of the ischemic thigh multiplied by 100. A qualitative assessment by observation of the arterial filling in the distal leg (saphenous and popliteal arteries) also was performed. For purposes of comparison among different treatment groups, the arterial filling was noted as present or absent.

Representative post-mortem angiograms obtained at day 1 after surgery demonstrated in AdCMV.VEGF$_{121}$-treated animals an increase in the number of vessels in the thigh compared to controls. For the saline group, 24 hours after femoral artery removal, there was very little collateral development, if any, visible in the thigh. In contrast, in the AdCMV.VEGF$_{121}$ group there was clearly a network of newly formed vessels sprouting mainly from the internal iliac artery towards the medial thigh. The resulting angiographic score was significantly higher for AdCMV.VEGF$_{121}$-treated animals showing a four-fold increase in the number of vessels compared to animals which received saline (AdCMV.VEGF$_{121}$=51±1, saline= 12±2, P<0.0001). Animals treated with AdCMV.Null also had a significantly higher angioscore than the saline group (Null=29±4, P<0.05 vs. saline), yet lower than the AdCMV.VEGF$_{121}$-treated group (P<0.001 vs. AdCMV.VEGF$_{121}$).

The qualitative angiographic assessment showed that not only were there more vessels in AdCMV.VEGF$_{121}$-treated animals, as indicated by the angiographic score, but also that these vessels invariably reestablished the flow to the more distal arteries in the leg (five out of five animals). Among animals that received AdCMV.Null, distal arterial filling in the ischemic leg was documented in two out of five animals, while none of the animals in the saline group exhibited a similar finding. Statistical analysis of these data showed that the AdCMV.VEGF$_{121}$ group was significantly different from the saline (P<0.002) and AdCMV.Null (P<0.05) groups, whereas the control groups were not different from each other (P=0.2).

This example therefore demonstrates the induction of angiogenesis or collateral blood formation in a nonischemic skeletal muscle at risk of being affected by, and subsequently affected by, ischemia or a vascular occlusion after treatment with a pharmaceutical composition comprising a DNA encoding an angiogenic peptide.

Example 2

This example demonstrates perfusion of blood in nonischemic skeletal muscle. In rats, the bioenergetic profile of the gastrocnemius muscle, as measured by $^{31}$P-NMR spectroscopy, was used as an indirect indicator of gastrocnemius muscle perfusion. Histology was also performed to determine the capillary and arteriole length densities in the skeletal muscles of the hindlimbs, another indirect indicator of the level of blood perfusion in the gastrocnemius muscle.

$^{31}$P-NMR Spectroscopy Protocol $^{31}$P-NMR spectroscopy was used to determine the bioenergetic profile of the gastrocnemius muscles of both hindlimbs at rest and during exercise induced by electrical stimulation of these muscles. NMR tests were conducted in twenty-two rats on days 1, 7, and 14 after surgery. All data were acquired on a 1.9-T/31-cm NMR spectrometer (Biospec, Bruker Medizintechnik GmbH, Ettlingen, Germany).

After animals were sedated with ketamine (60 mg/kg) and xylazine (10 mg/kg), two platinum subdermal electrodes (Grass Instruments Manufacturing, Braintree, Mass.) were inserted in the proximal head of the gastrocnemius and in the Achilles' tendon, respectively, for electrical stimulation. An elliptical radio-frequency (RF) surface coil tuned to the $^{31}$P-resonance frequency, especially built for this study, was applied against the gastrocnemius. The electrodes were then connected to a high-voltage programmable stimulator (Model S-10, Grass Instruments Manufacturing, Braintree, Mass.) with an isolation transformer (Grass Instruments Manufacturing, Braintree, Mass.) via a low-pass filter. The foot of the stimulated leg was tied to a strain gauge force transducer (Grass Instruments Manufacturing, Braintree, Mass.) using a 3-0 silk suture. The force transducer was connected to a strain gauge conditioner, preamplifier, and chart recorder (Gould Instrument Systems, Inc., Cleveland, Ohio), allowing continuous monitoring of the muscle contraction force during the electrical stimulation.

The electrical stimulation was applied as a train of pairs of pulses of 100 µs length separated by a 200 ms interval and repeated once every two seconds. The voltage of these pulses was incremented over about thirty seconds until the observed contraction force no longer increased, thereby determining the stimulation voltage for that leg. The animal was positioned in the NMR magnet, and the surface coil tuning was adjusted for exact resonance. Radio-frequency pulses were applied every two seconds with adiabatic frequency and amplitude shaping to compensate for the surface coil's RF inhomogeneity. The proton NMR signal from the coil was detected and used as a guide to magnetic field shipping for $^{31}$P-spectroscopy. The exact proton resonance frequency of the water peak was used to calculate the expected frequency for $^{31}$P, based on the gyromagnetic ratios of the two nuclei. The RF transmitter was set to the calculated $^{31}$P frequency, and a preliminary $^{31}$P spectrum was recorded with a one-minute acquisition time.

In each NMR experiment, one spectrum (requiring two minutes of data acquisition time for 64 scans) was collected immediately prior to stimulation, three 2-minute spectra were collected during stimulation, and six 2-minute NMR acquisitions were collected right after stimulation. Thus, for each leg, ten NMR spectra were recorded. After the experiment was completed, the procedure was repeated for the other leg, beginning with administration of additional anesthetic and placement of the subdermal electrodes.

The NMR spectra resulting from these experiments were processed to yield PCr/(PCr+Pi) ratios as a function of time before, during, and after stimulation. After linebroadening and Fourier transformation, each spectrum was manually phased and its baseline was corrected using a spline fit with manual knot selection. Integration limits were selected by hand for the creatine phosphate and inorganic phosphate resonances, and an automated routine was used to generate a list of integrals, peak heights, and peak frequencies. The resulting data was used to calculate PCr/(PCr+Pi) ratios for peak heights. PCr/(PCr+Pi) data were plotted against a time axis ranging from zero to twenty minutes, beginning with the 2-minute data acquisition prior to electrical stimulation in which the control spectrum was recorded.

Figure 3A:
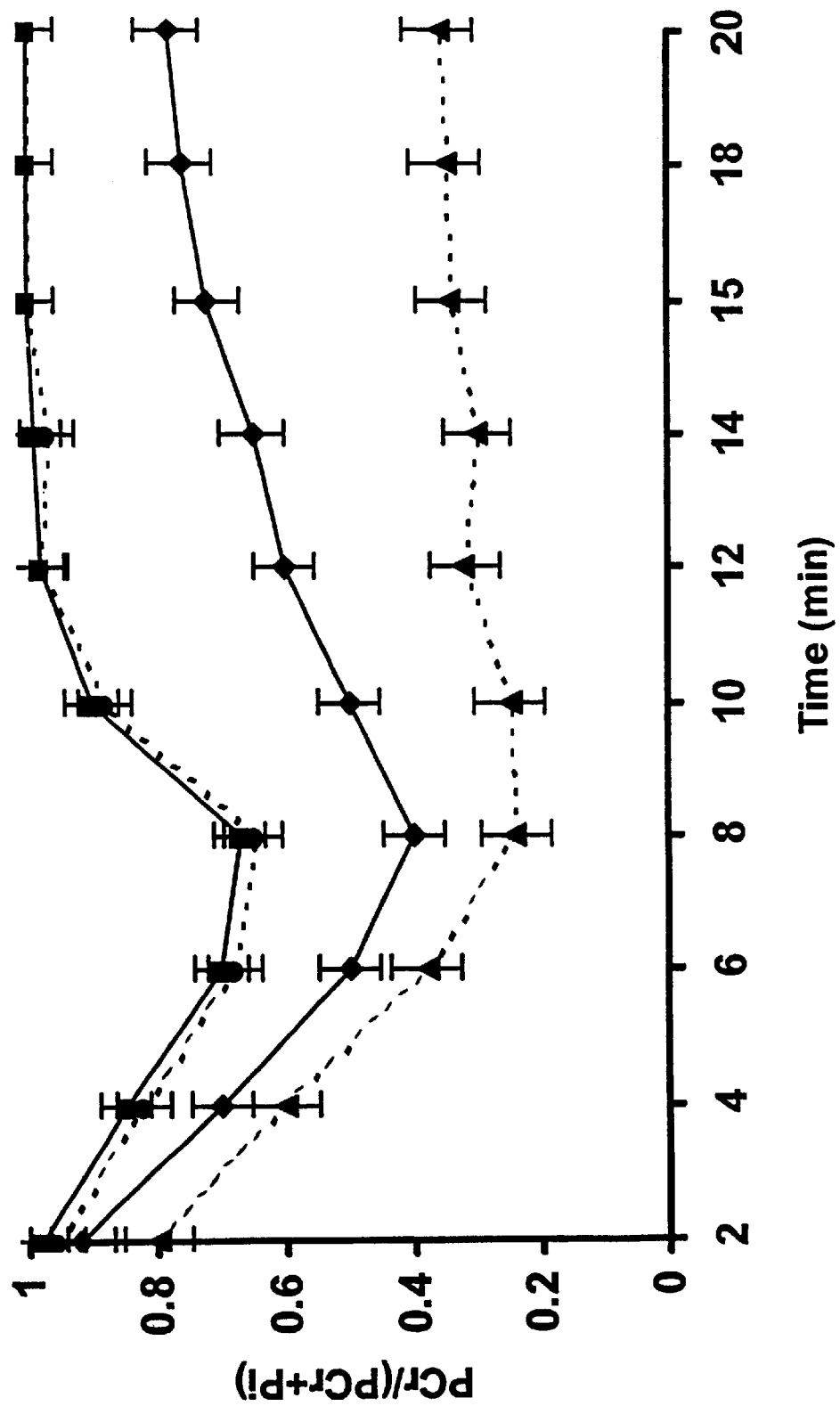
FIGS. 3A–3C are graphs of $^{31}$P nuclear magnetic resonance (NMR) spectroscopy data showing the PCr/(PCr+Pi) ratio of the gastrocnemius muscle as a function of electrical stimulation protocol time (min).
Figure 3B:
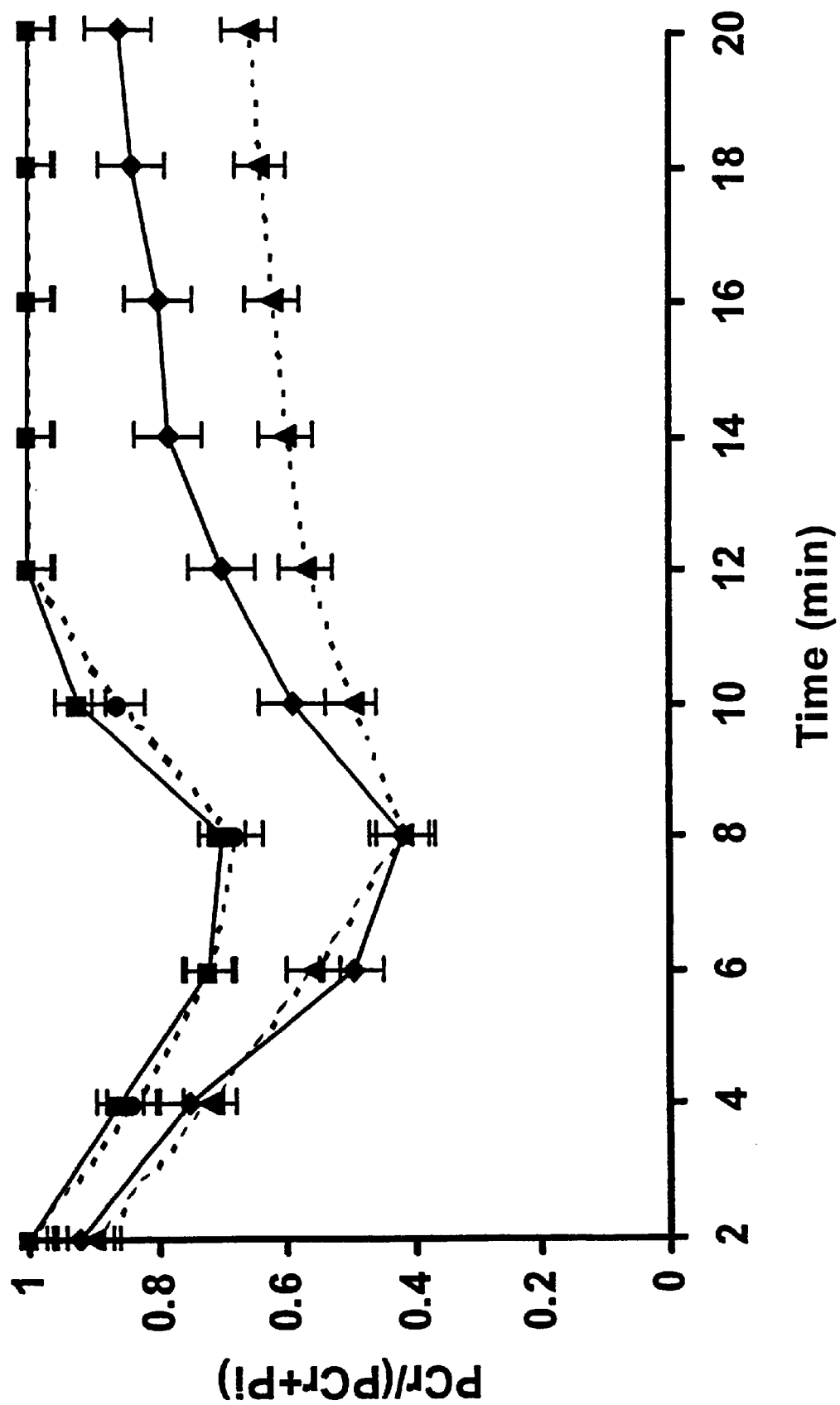
Figure 3C:
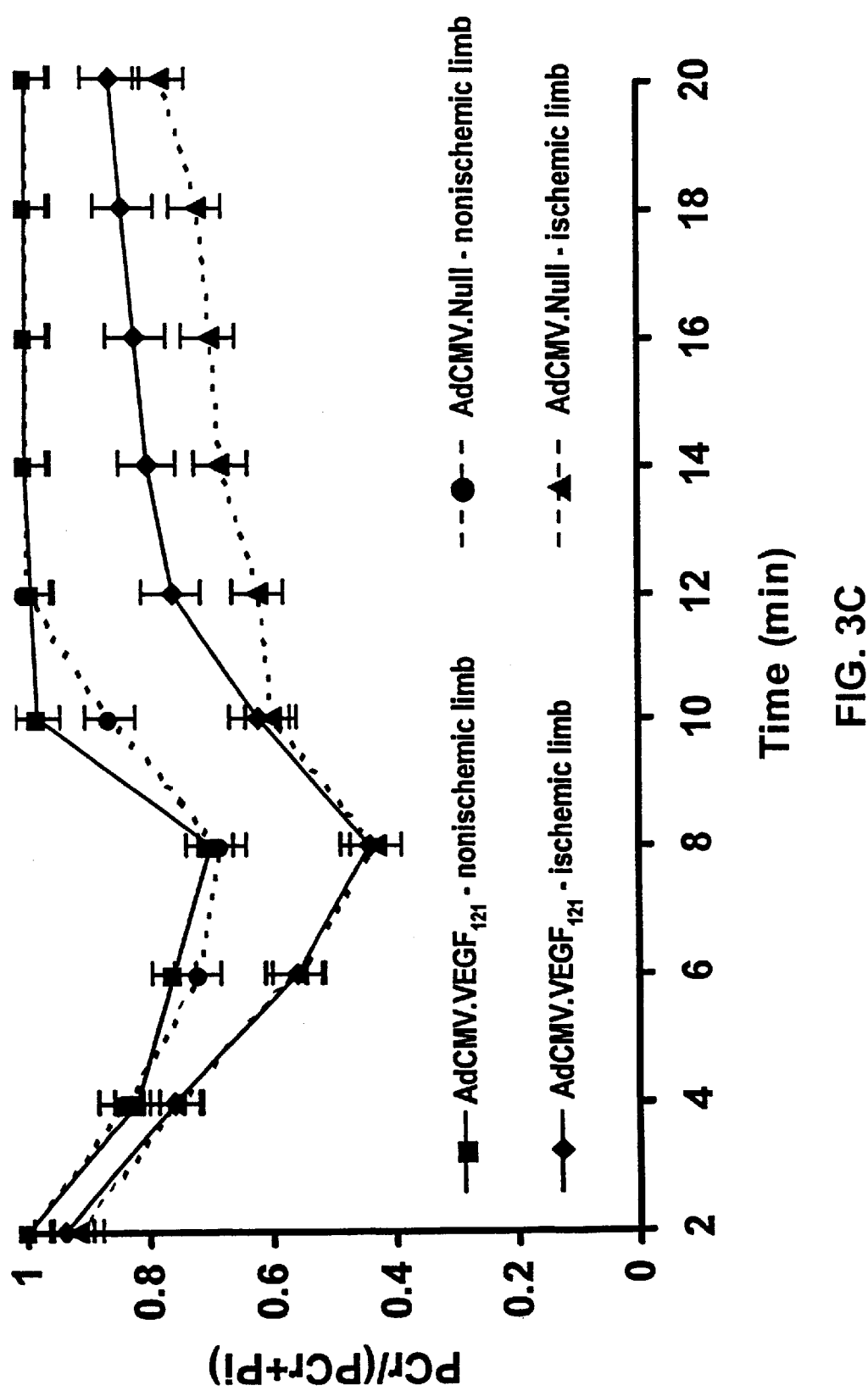

FIGS. 3A–C, which collectively are graphs of NMR data (PCr/(PCr+Pi)) obtained in rats as a function of time after surgery, show: At day 1, AdCMV.VEGF$_{121}$ pre-treated ischemic limbs recovered approximately 0.8 of the original PCr/(PCr+Pi), and AdCMV.Null pre-treated ischemic limbs only recovered approximately 0.3 of the original PCr/(PCr+Pi) (see FIG. 3A). At day 7, AdCMV.VEGF$_{121}$ pre-treated ischemic limbs recovered approximately 0.8 of the original PCr/(PCr+Pi), and AdCMV.Null pre-treated ischemic limbs recovered approximately 0.6 of the original PCr/(PCr+Pi) (see FIG. 3B). At day 14, AdCMV.VEGFI$_{121}$ and AdCMV.Null pre-treated ischemic limbs recovered approximately 0.8 of the original PCr/(PCr+Pi) (see FIG. 3C). Animals pre-treated with AdCMV.VEGF$_{121}$ showed an improved bioenergetic profile of the gastrocnemius muscle after femoral artery removal when compared to controls. At day 1 after surgery, pre-exercise PCr/(PCr+Pi) ratio of the ischemic limb in AdCMV.VEGF$_{121}$-treated animals was not different from the nonischemic limb. There also was less reduction of the PCr/(PCr+Pi) ratio during the stimulation (exercise) phase and faster and more complete restoration of that ratio in the recovery phase in AdCMV.VEGF$_{121}$-treated animals than controls (P<0.0001). The faster recovery of AdCMV.VEGF$_{121}$-treated animals persisted at day 7 (P<0.004) but not at day 14 (P>0.1) after surgery since the control animals eventually recovered enough to make this difference non-significant.

Histology and Morphometric Analysis

To evaluate the angiogenic effect of AdCMV.VEGF$_{121}$ in the absence of ischemia at the capillary level, fourteen rats were injected either with AdCMV.VEGF$_{121}$ (2×10$^9$ pfu/ml) or AdCMV.Null (2×10$^9$ pfu/ml), as previously described. Fifteen days after injection of the viral vector, animals were anesthetized as usual, and a median laparotomy was performed. Both legs were then perfused via the abdominal aorta with 10% buffered formalin at 100 mm Hg for fifteen minutes. Subsequently, the adductor and gastrocnemius muscles were immersion-fixed in formalin for 48 hours.

After paraffin embedding, sections from each sample were cut in 3 μm thick slices so that the muscle fibers were oriented in a transverse direction, and stained with -smooth muscle actin antibody, thereby allowing for the identification of smooth muscle cells in the vascular wall. By this approach, it was possible to identify arterioles and differentiate them from capillaries and veins, because the thin walls of these vessels do not contain smooth muscle cells.

Sections were deparafinized, rinsed in phosphate buffered saline (PBS), incubated at 37° C. for sixty minutes with mouse monoclonal anti- -smooth muscle actin (clone IA4, Sigma Chemical Co., St. Louis, Mo.) diluted 1:30 in PBS, and subsequently incubated at 37° C. for sixty minutes with anti-mouse IgG tetramethyrhodamine B isothiocyyanate (TRITC) labeled antibody, diluted 1:60 in PBS. Finally, sections were rinsed in PBS and embedded in Vectashield (Vector Laboratories, Burlingame, Calif.) mounting medium.

For the morphometric analysis, the total area of the muscle present in each section was examined at ×200 magnification. In each field examined, measurements of the profiles of any artery and arteriole included the length of its major and minor luminal diameter and wall thickness along the minor axis. The morphometric analysis allows the estimate of the length density of vessels arranged in any variety of orientations. This methodology is based on the evaluation of each vascular profile individually as it is encountered. Specifically, for n profiles counted in an area A, the length density Ld is equal to the sum of the ratio of the major or long axis to the minor or wide axis of each profile. Thus, Ld is equal to the length per unit volume in the same dimensional area: $Ld=1/A\Sigma=(R_1+R_2+R_3+ \ldots R_n)/A$, where arteriole length density was expressed per unit volume (mm/mm$^3$) of muscle.

The analysis of the capillary network was performed utilizing an ocular reticle (10,0001 μm$^2$ area) at ×1,000 magnification. Sections from each sample were cut in 3 μm thick slices and were stained with hematoxylin and eosin. The number of capillary profiles ($n_{cap}$) was measured in an area of tissue section (A) in which muscle fibers were cut transversely. The number of transversely oriented capillaries per unit area is equal to their length per unit volume. In each section, seventy-five fields were randomly examined. The number of capillary profiles was counted to compute the capillary numerical density per mm$^2$ of muscle. $n_{cap}/mm^2$= $n_{cap}$ in total fields/total area.

Figure 4A:
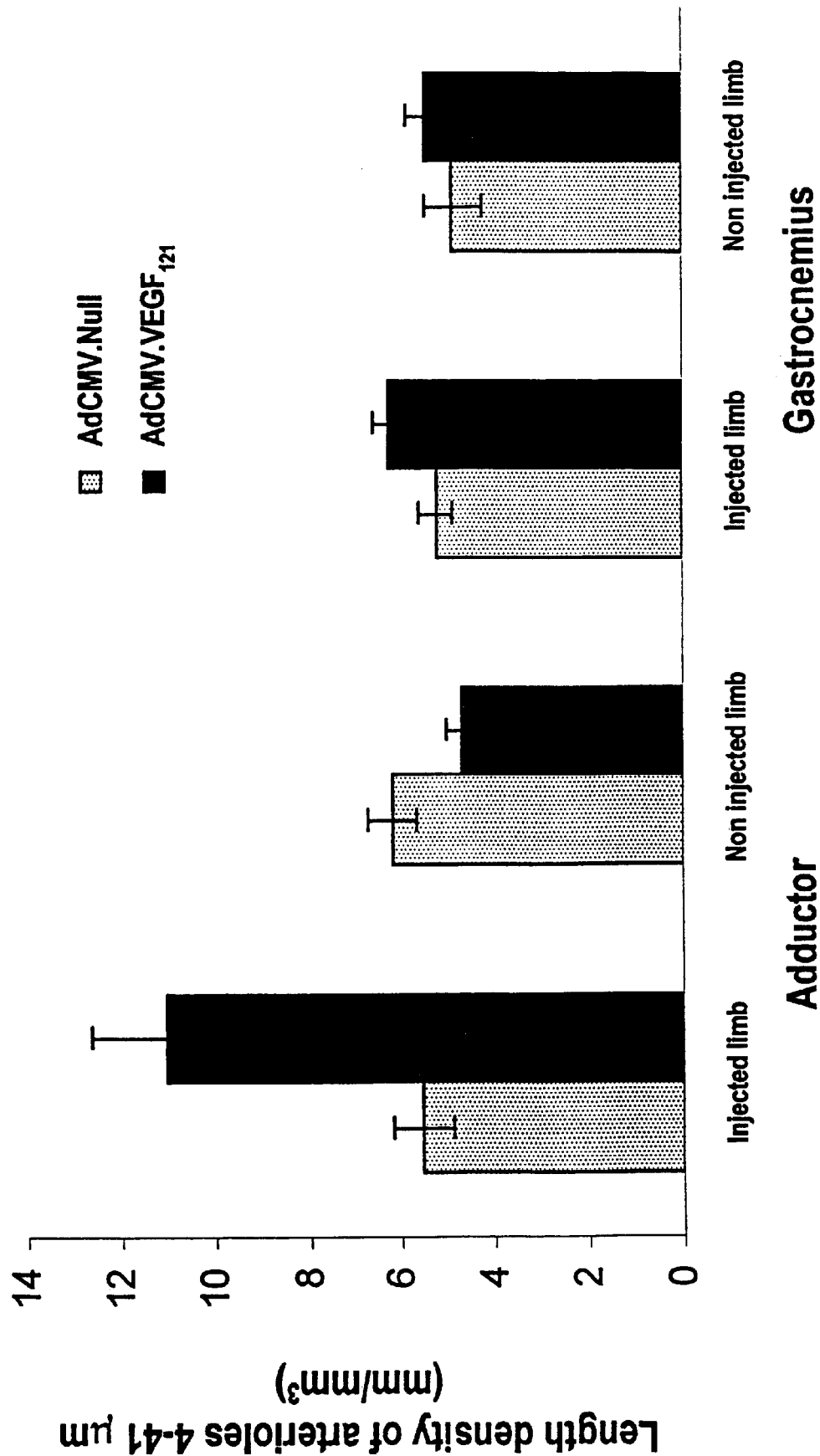
FIGS. 4A and 4B are bar graphs of blood vessel length density (mm/mm$^3$) in the adductor and gastrocnemius muscles of both injected and non-injected hindlimbs treated with AdCMV.VEGF$_{121}$ and AdCMV.Null (control)
Figure 4B:
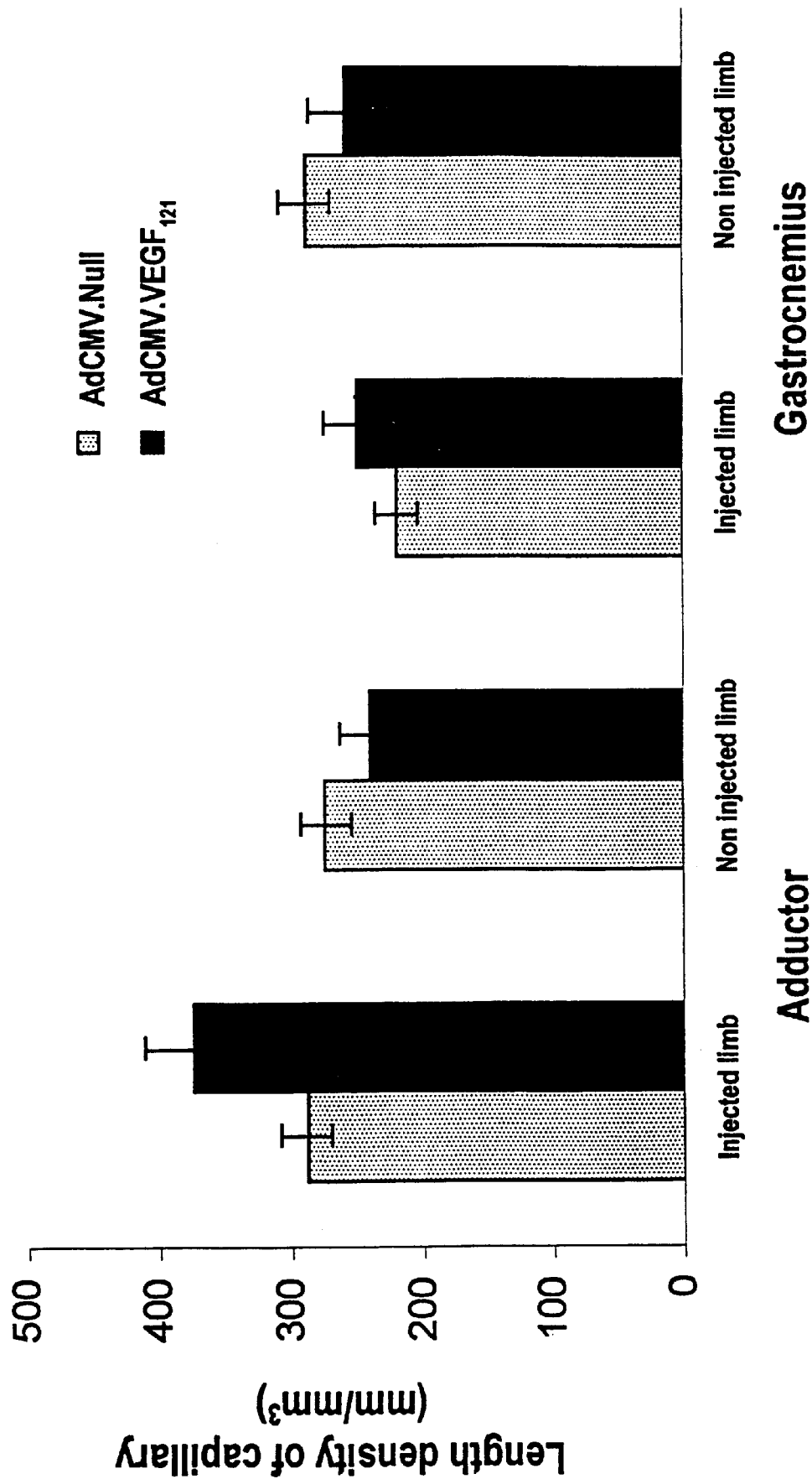

FIG. 4A, which is a graph of arteriole length densities in the adductor and gastrocnemius muscles of both hindlimbs, shows that the length density in the adductor muscle was approximately 11 mm/mm$^3$ for the limb injected with AdCMV.VEGF$_{121}$ and approximately 5 mm/mm$_3$ for the limb injected with AdCMV.Null, while, for the gastrocnemius muscle, the length density of the injected limb was approximately 6 mm/mm$^3$ for AdCMV.VEGF$_{121}$ and 5 mm/mm$^3$ for AdCMV.Null. FIG. 4B, which is a graph of capillary length densities in the adductor and gastrocnemius muscles of both hindlimbs, shows that the length density in the adductor muscle was approximately 350 mm/mm$^3$ for the limb injected with AdCMV.VEGF$_{121}$ and approximately 300 mm/mm$^3$ for the limb injected with AdCMV.Null, while, for the gastrocnemius muscle, the length density of the injected limb was approximately 250 mm/mm$^3$ for AdCMV.VEGF$_{121}$ and 275 mm/mm$^3$ for AdCMV.Null.

Histological analysis of the muscle sections of the ischemic limb revealed that in AdCMV.VEGF$_{121}$-treated rats there was a 96% increase in the length density of arterioles 4–41 μm diameter (P<0.008). The wall thickness of these arterioles was 3.24±0.35 μm and 3.54±0.15 μm for AdCMV.VEGF$_{121}$ and AdCMV.Null-injected tissues, respectively (P=ns). Additionally, there was a 29% increase in the capillary length density of the adductor muscles injected with AdCMV.VEGF$_{121}$ vs. AdCMV.Null (P<0.03). It is noteworthy that in the limbs treated with AdCMV.VEGF$_{121}$ the angiogenic effect was limited to the muscle tissue directly injected with the adenoviral vector and there was no evidence of an increase in arterioles and capillary length densities (P=ns) in the gastrocnemius muscle of the same limbs.

This example demonstrates the maintenance or enhancement of perfusion of blood to a nonischemic skeletal muscle at risk of being affected by, and subsequently affected by, ischemia or a vascular occlusion, after treatment with a pharmaceutical composition comprising a DNA encoding an angiogenic peptide.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for enhancing the level of perfusion of blood to a nonischemic skeletal muscle at risk of suffering from ischemic damage or at risk of being affected by a vascular occlusion comprising directly administering to a nonischemic skeletal muscle a pharmaceutical composition comprising (a) a pharmaceutically acceptable carrier and (b) a DNA encoding an angiogenic peptide, such that the level of perfusion of blood to the nonischemic skeletal muscle is enhanced.

2. The method of claim 1, wherein the nonischemic skeletal muscle is at risk of suffering from ischemic damage.

3. The method of claim 2, wherein the enhanced level of perfusion of blood to the nonischemic skeletal muscle is maintained upon induction of ischemia to the skeletal muscle.

4. The method of claim 1, wherein the nonischemic skeletal muscle is at risk of being affected by a vascular ócclusion.

5. The method of claim 4, wherein collateral blood vessel formation is induced in the nonischemic skeletal muscle.

6. The method of claim 1, wherein angiogenesis is induced in the nonischemic skeletal muscle.

7. The method of claim 1, wherein the angiogenic peptide is a vascular endothelial growth factor (VEGF).

8. The method of claim 7, wherein the angiogenic peptide is selected from the group consisting of VEGF$_{121}$, VEGF$_{145}$, VEGF$_{165}$, and VEGF$_{189}$.

9. The method of claim 1, wherein the DNA encoding an angiogenic peptide is in a viral vector.

10. The method of claim 9, wherein the viral vector is a replication deficient adenoviral vector.

11. The method of claim 10, wherein the adenoviral vector is deficient in at least one essential gene function of the E1 region of the adenoviral genome.

12. The method of claim 10, wherein the adenoviral vector is deficient in at least part of the E3 region.

13. The method of claim 11, wherein the adenoviral vector has at least a partial deletion of the E1a region, at least a partial deletion of the E1b region, and at least a partial deletion of the E3 region.

14. The method of claim 10, wherein the adenoviral vector is deficient in at least one essential gene function of the E4 region of the adenoviral genome.

15. The method of claim 14, wherein the adenoviral vector has at least a partial deletion of the E1 region, at least a partial deletion of the E3 region, and at least a partial deletion of the E4 region.

16. The method of claim 10, wherein the DNA is oriented from right to left in the adenoviral genome of the adenoviral vector.

17. The method of claim 10, wherein the DNA is positioned in the E1 region of the adenoviral genome.

18. The method of claim 1, wherein the skeletal muscle comprises a portion of a human limb.

* * * * *